(12) United States Patent
Hussain et al.

(10) Patent No.: US 6,737,041 B1
(45) Date of Patent: May 18, 2004

(54) NON-OZONE DEPLETING VAPOCOOLANTS

(75) Inventors: Ajaz S. Hussain, Cincinnati, OH (US); Rakesh Govind, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 1,826 days.

(21) Appl. No.: 08/110,115

(22) Filed: Aug. 20, 1993

(51) Int. Cl.$^7$ .......................... A61K 7/22; A61K 31/01; A61K 31/045; A61K 31/12
(52) U.S. Cl. .......................... 424/45; 514/762; 514/724; 514/675; 514/692
(58) Field of Search .......................... 424/45; 514/762, 514/724, 675, 692; 128/DIG. 27

(56) References Cited

U.S. PATENT DOCUMENTS

| | | | | |
|---|---|---|---|---|
| 4,198,313 A | * | 4/1980 | Bargigia et al. | 252/305 |
| 4,646,735 A | * | 3/1987 | Seney | 128/303.1 |
| 4,865,028 A | | 9/1989 | Swart | 128/303.1 |
| 5,039,485 A | | 8/1991 | Conviser et al. | 422/34 |
| 5,330,745 A | * | 7/1994 | McDow | 424/45 |

OTHER PUBLICATIONS

114CA:1087084 Heiskel et al. 1991.*
Remmington's Pharmaceutical Science 17$^{th}$ Ed 1985 p. 1307.*

DuPont Chemicals MSDS Material Safety Data Sheet 2187FR Revised Sep. 21, 1992, Printed Dec. 23, 1992, "SUVA" Cold–MP ps. 1–5.

PDD–7301—Pharmaceutical Research vol. 8, No. 10, 10–91—Supplement PHREEB 8(10)SI—S350–(1991).

CFC Propellant Substitution International Perspectives— F.X. Fischer, et al, Pharmaceutical Tech. (9–89), pp. 44, 48, 50, 52.

CFC Propellant Substitution P–134a as a Potential Replacement for P–12 in MDI's—Richard N. Dalby et al. Pharmaceutical Tech. (3–90) pp. 26, 28, 30.

* cited by examiner

*Primary Examiner*—Russell Travers
(74) *Attorney, Agent, or Firm*—Frost Brown Todd LLC

(57) ABSTRACT

Chemical compositions are provided, for use as topical anesthetics or skin refrigerants. These compositions do not cause the depletion of the stratospheric ozone layer and are non-toxic, non-carcinogenic and less flammable than ethyl chloride. Also these chemical compositions match the skin temperature versus time profile needed in the management of myofascial pain syndromes, for effectively freezing skin prior to minor skin surgery and for effectively freezing skin prior to giving painless injections.

11 Claims, No Drawings

NON-OZONE DEPLETING VAPOCOOLANTS

FIELD OF THE INVENTION

The present invention relates generally to chemical compositions for use as topical anesthetics or skin refrigerants. More specifically, this invention provides chemical compositions for use as topical anesthetics or skin refrigerants, which compositions do not cause the depletion of the stratospheric ozone layer and are non-toxic. Even more specifically, this invention provides chemical compositions for use as topical anesthetics or skin refrigerants, which compositions, in addition to having the above properties, match the skin temperature versus time profile needed, in the management of myofascial pain syndromes, for effectively freezing skin prior to minor skin surgery and for effectively freezing skin for giving painless injections.

BACKGROUND OF THE INVENTION

The term vapocoolants will be understood to include topical anesthetics, skin refrigerants and the like. Vapocoolants are volatile liquid compositions which exert high pressure in a container at room temperature. When a container having such compositions is inverted and opened, in the proximity of human skin, the liquid is immediately expelled out of the bottle in a stream and starts evaporating. The evaporation of the liquid cools the liquid stream by the time it impacts the skin. The liquid on the skin continues to evaporate and remove heat from skin resulting in the rapid decline of the skin temperature.

The above-described effect of skin cooling is well known in the art. U.S. Pat. No. 4,865,028 to Swart et al. issued Sep. 12, 1989 describes a method for the therapeutic treatment of the skin of a human or animal by the freezing of the skin by application of a refrigerant thereto wherein the refrigerant is applied through a cotton wool bud which encompasses the discharge end of the supply tube and which cotton wool bud surrounds the outlet of the supply tube. In fact, the '028 patent lists several refrigerants which may be suitable for use in the method of the '028 patent. In this regard, several hydrofluorocarbons are disclosed such as tetrafluoromethane, trifluoromethane, hexafluoroethane, monobromotrifluoromethane, and 1,1-difluoroethane. It is also mentioned in the '028 patent that all of these listed hydrofluorocarbons are "often environmentally harmful." Thus, the '028 patent in fact points away from the use of 1,1-difluoroethane (152a).

However, when the '028 patent refers to the environmentally deleterious effects of hydrofluorocarbons (HFC's) the reference is to effects such as the greenhouse effect. It is well known that hydrofluorocarbons or HFC's have no ozone depletion potential whatsoever. On the other hand, compounds such as hydrochlorofluorocarbons (HCFC's) and chlorofluorocarbons (CFC's) are considered to be ozone depleting.

In fact, vapocoolants have been on the market since the 1940's and have been known since that time. The most widely used commercial products are Fluorimethane® (The Gebauer Company, Cleveland, Ohio) and ethyhlchloride. Fluorimethane® is used for management of myofascial pain syndrome using the well-known spray and stretch technique (See Manyel J. M.: "Spray and Stretch treatment for myofascial pain"; Hospital Physician, 1973). Ethylchloride is used for pain control in pain associated with injections or contusions. While it is acknowledged that vapocoolants in general have been on the market since the 1940's, the present invention is directed to the specific development of chemical compositions which are non-ozone depleting and non-toxic, while at the same time having a skin temperature-time profile similar to that obtained upon application of the currently widely available products such as Fluorimethane® and ethylchloride.

The '028 patent also discloses in its specification, Dutch patent application No. 7,308,008, wherein the use of a liquid refrigerant with a low boiling point for carrying out cryo-surgical treatments, such as the removal of an eye lens affected by cataract and cataract operation is disclosed. However, the use of compositions of the present application is not for cryosurgery, but for the specific applications included herein.

U.S. Pat. No. 5,039,485 issued Aug. 13, 1991 to Conviser et al. discloses a sterilant mixture comprising 14–25 mole percent ethylene oxide and 75–86 mole percent 1,1,2,2-pentofluoroethane, and a sterilization method using the same. The '485 patent is relevant in that it recognizes the problem associated with the use of CFC's, i.e., the resultant damage to the stratospheric ozone layer. It is also disclosed in the '485 patent that 1,2,2,2-tetrafluoroethane (HFC 134a), does not increase the ozone depletion potential of a certain sterilant mixture.

The currently marketed vapocoolants described above (Fluorimethane® and ethylchloride), are intended for topical application in the management of myofascial pain, restricted motion, muscle spasms and for the control of pain associated with injections. Fluorimethane® is classified as a prescription drug and is regulated by the United States Food and Drug Administration (FDA). It was formulated by Dr. Janet Travell in the late 1950's and since then has been widely used for the management of the above conditions and symptoms. It is a mixture of two CFC's, namely dichlorodifluoromethane—15% and trichloromonofluoromethane—85%. Chlorofluorocarbons are known to be extremely harmful to the stratospheric ozone layer and in accordance with the Montreal Protocol of September 1987, have to be phased out along with all other CFC's by the year 2000. The present invention offers new chemical compositions that match the skin temperature-time profile of Fluorimethane® and ethyl chloride, which compositions do not contain CFC's and which are non-toxic.

Ethylchloride has been found to be carcinogenic, hepatotoxic and is also known to be highly flammable. The present invention makes it possible to replace ethylchloride with a non-ozone depleting vapocoolant which shows the temperature time characteristics of ethylchloride and Fluorimethane® and which is simultaneously non-toxic and non-carcinogenic in comparison to ethylchloride. The present chemical compositions are also not as flammable as ethyl chloride.

SUMMARY OF THE INVENTION

It is a primary object of the present invention to provide a chemical composition for use as a vapocoolant, which vapocoolant does not cause the depletion of the stratospheric ozone layer and which is non-toxic.

It is another object of the present invention to provide a vapocoolant having the above described characteristics and which has a skin temperature versus time profile suitable for management of myofascial pain syndromes, for effectively freezing skin prior to minor skin surgery and for effectively freezing skin prior to giving painless injections.

It is a further object of the present invention to provide chemical compositions which have similar skin temperature versus time profiles as compared to currently available vapocoolants for similar purposes.

It is yet another object of the present invention to provide chemical compositions which are non-toxic in comparison to ethylchloride.

A still further object of the present invention is to provide chemical compositions for the purposes described above and having the characteristics described above, which compositions are not carcinogenic.

A further object of the present invention is to provide chemical compositions for the above described purposes and having the above described characteristics, which compositions are less flammable than ethylchloride.

Yet another object of the present invention is to provide chemical compositions for the above described purposes and having the above described characteristics, so as to be effective in replacing the presently used chlorofluorocarbon vapocoolants, which CFC's are to be phased out by the year 2000.

In accordance with the invention, there is provided a non-ozone depleting, non-toxic and non-carcinogenic vapocoolant liquid chemical compostion for use in localized cooling of a desired area of the skin of humans and other animals, said composition comprising by total weight of the composition 40 to 55% hydrofluorocarbon and 60 to 45% of ethyl alcohol; and being capable of cooling said desired area to at least as low as approximately minus 5° C., upon spraying of said composition onto said desired area, from a predetermined distance for a maximum of 5 seconds.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION OF THE PREFERRED EMBODIMENT

In accordance with the preferred embodiment of the present invention, the present invention will now be described in detail in connection with the use of chemical compositions for the cooling of a specific area of the skin in a human subject. It is to be understood that the compositions of the present invention have equal application in the management of the specific applications described above, namely myofascial pain, restricted motion, muscle spasms and for freezing skin prior to minor skin surgery. It is also to be understood that the present compositions are not restricted to any particular kind of delivery system of the vapocoolants such as a particular bottle, can or other packaging container. Futhermore, the skin of animal subjects other than human subjects, may also be cooled using the vapocoolants of the present invention.

The following HFC's are considered to satisfy the criteria required by the compositions of the present invention, namely that the components be non-ozone depleting, non-toxic, non-carcinogenic and less flammable than ethyl chloride and that the resulting chemical composition/mixture have a skin temperature-time profile comparable to that obtained upon application of the currently commercially available CFC based product Fluorimethane® and ethyl chloride:

1,1-difluoroethane (HFC 152a)
1,1,1,2-tetrafluoroethane (HFC 134a)

The above disclosed HFC's are typically mixed with ethyl alcohol, the HFC's being present in the range of 40–55 weight percent and ethyl alcohol in the range of 60 to 45 weight percent. The ethyl alcohol used in these mixtures, may or may not include a denaturing agent such as isopropyl alcohol, acetone or camphor.

Detailed tests were conducted with respect to mixtures of: (a) 1,1-difluoroethane (HFC 152a) and ethyl alcohol and (b) 1,1,1,2-tetrafluoroethane (HFC 134a) and ethyl alcohol.

The general procedure for the testing of the compositions of the present invention involved the following: spray skin from a distance of about 12 inches continuously for the desired amount of time, typically from 3 to 5 seconds, but do not frost the skin.

The following tables, I–VIII describe the result of studies 1 and 2.

TABLE I

Experimental conditions for study 1

1. Spray distance: 12 inches
2. Spay time: 5 seconds
3. Coolants:
   Ethyl chloride at room temperature, denoted by EC
   Ethyl chloride at 11° C., denoted by ECC
   Fluorimethane ® at room temperature, denoted by FM
   Fluorimethane ® at 11° C., denoted by FMC
   Mixture of 45% HFC 152a and 55% ethyl alcohol, denoted by EI
   Mixture of 50% HFC 134a and 50% ethyl alcohol, denoted by EII
   Mixture of 55% HFC 134a and 45% ethyl alcohol, denoted by EIII

TABLE II

| Code | Sex | Race | Age | Weight | Height | Skin T |
|---|---|---|---|---|---|---|
| 1 | F | Black | 45 y | 155 lb | 5'7" | 30.0 |
| 2 | F | White | 28 y | 110 lb | 5'1" | 32.0 |
| 3 | F | Asian | 28 y | 90 lb | 5'0" | 32.5 |
| 4 | M | White | 28 y | 163 lb | 6'0" | 33.2 |
| 5 | M | White | 35 y | 210 lb | 6'0" | 32.0 |

TABLE III

Minimum temperature for site A
(a site on the subject's forearm)

| COOL-ANT | SUB-JECT 1 | SUB-JECT 2 | SUB-JECT 3 | SUB-JECT 4 | SUB-JECT 5 | MEAN ± STANDARD DEVIATION |
|---|---|---|---|---|---|---|
| EC | −13.22 | −16.87 | −17.56 | −11.72 | −15.26 | −14.93 ± 2.45 |
| ECC | −15.80 | −11.32 | −17.81 | −16.19 | −16.84 | −15.59 ± 2.50 |
| FM | −17.34 | −17.24 | −16.43 | −15.18 | −15.86 | −16.41 ± 0.92 |
| FMC | −16.75 | −17.85 | −19.35 | −14.14 | −23.30 | −18.28 ± 3.40 |
| EI | −20.10 | −17.05 | −16.65 | −17.43 | −15.19 | −17.29 ± 1.79 |
| EII | −17.29 | −15.03 | −14.99 | −13.62 | −16.32 | −15.45 ± 1.40 |
| EIII | −17.91 | −19.33 | −19.83 | −17.65 | −21.89 | −19.32 ± 1.70 |

TABLE IV

Minimum temperature for site B
(a site on the subject's forearm, different from A)

| COOL-ANT | SUB-JECT 1 | SUB-JECT 2 | SUB-JECT 3 | SUB-JECT 4 | SUB-JECT 5 | MEAN ± STANDARD DEVIATION |
|---|---|---|---|---|---|---|
| EC | −16.87 | −15.78 | −15.73 | −16.12 | −17.50 | −16.40 ± 0.77 |
| ECC | −19.22 | −15.56 | −18.71 | −17.80 | −20.75 | −18.41 ± 1.92 |
| FM | −20.39 | −15.39 | −16.62 | −13.92 | −16.27 | −16.52 ± 2.40 |

TABLE IV-continued

Minimum temperature for site B
(a site on the subject's forearm, different from A)

| COOL-ANT | SUB-JECT 1 | SUB-JECT 2 | SUB-JECT 3 | SUB-JECT 4 | SUB-JECT 5 | MEAN ± STANDARD DEVIATION |
|---|---|---|---|---|---|---|
| FMC | −15.87 | −16.76 | −19.34 | 19.51 | −20.21 | −18.34 ± 1.91 |
| EI  | −18.59 | −21.25 | −15.65 | −17.85 | −19.73 | −18.62 ± 2.09 |
| EII | −13.77 | −16.18 | −12.97 | −17.80 | −17.67 | −15.68 ± 2.22 |
| EIII | −17.34 | −18.17 | −18.54 | −23.92 | −22.63 | −20.12 ± 2.95 |

TABLE V

Experimental conditions for study 2

1. Spray distance: 12 inches
2. Spay time: 3 seconds
3. Coolants:
    Ethyl chloride at room temperature, denoted by EC
    Ethyl chloride at 11° C., denoted by ECC
    Fluorimethane ® at room temperature, denoted by FM
    Fluorimethane ® at 11° C., denoted by FMC
    Mixture of 45% HFC 152a and 55% ethyl alcohol, denoted by EI
    Mixture of 50% HFC 134a and 50% ethyl alcohol, denoted by EII
    Mixture of 52% HFC 134a and 48% ethyl alcohol, denoted by EIII
    Mixture of 55% HFC 134a and 45% ethyl alcohol, denoted by EIV

TABLE VI

| Code | Sex | Race | Age | Weight | Height | Skin T |
|---|---|---|---|---|---|---|
| 1 | M | Asian | 25 y | 125 lb | 5'7" | 32.5 |
| 2 | F | White | 37 y | 180 lb | 5'10" | 32.6 |
| 3 | F | White | 49 y | 240 lb | 5'4" | 32.0 |
| 4 | F | White | 56 y | 170 lb | 5'6" | 30.5 |
| 5 | F | Asian | 28 y | 90 lb | 5'0" | 32.5 |
| 6 | M | White | 28 y | 163 lb | 6'0" | 33.2 |
| 7 | F | White | 30 y | 123 lb | 5'6" | 34.0 |
| 8 | F | White | 31 y | 160 lb | 5'7" | 32.5 |
| 9 | M | Black | 43 y | 175 lb | 6'1" | 34.0 |
| 10 | M | White | 38 y | 200 lb | 5'10" | 33.0 |
| 11 | M | White | 30 y | 210 lb | 6'1" | 33.0 |
| 12 | F | White | 54 y | 165 lb | 5'10" | 30.9 |
| 13 | F | White | 34 y | 115 lb | 5'0" | 32.5 |
| 14 | F | White | 22 y | 140 lb | 5'9" | 31.5 |
| 15 | F | White | 44 y | 138 lb | 5'4.5" | 30.5 |

TABLE VII

Minimum temperature for site A (a site on the subject's forearm)

| CODE | EC | ECC | FM | FMC | EI | EII | EIII | EIV |
|---|---|---|---|---|---|---|---|---|
| 1 | −16.93 | −17.89 | −16.72 | −18.24 | −17.72 | −15.24 | 17.59 | −17.58 |
| 2 | −14.64 | −17.54 | −15.35 | −16.41 | −15.67 | −21.06 | −16.74 | −21.43 |
| 3 | −13.78 | −14.82 | −16.58 | −16.04 | −16.85 | −13.75 | −18.23 | −20.10 |
| 4 | −14.86 | −13.46 | −19.01 | −17.74 | −14.70 | −13.93 | −18.89 | −18.87 |
| 5 | −15.34 | −17.04 | −16.36 | −17.14 | −12.92 | −10.27 | −15.76 | −12.70 |
| 6 | −14.75 | −17.18 | −11.35 | −16.13 | −16.12 | −11.83 | −14.45 | −13.82 |
| 7 | 16.70 | −13.22 | −15.71 | −15.66 | −16.28 | −11.65 | −16.72 | −14.93 |
| 8 | −18.76 | −13.10 | −19.08 | −19.86 | −18.10 | −15.41 | −13.56 | −17.10 |
| 9 | −15.46 | −18.11 | −11.51 | −18.29 | −13.55 | −15.90 | −15.88 | −20.42 |
| 10 | −16.53 | −17.63 | −16.03 | −18.77 | −19.53 | −18.11 | −18.58 | −26.49 |
| 11 | −14.68 | −15.56 | −15.26 | −18.61 | −23.28 | −18.04 | −14.35 | −19.14 |
| 12 | −13.59 | −17.00 | −15.82 | −16.68 | −21.55 | −15.44 | −18.88 | −21.62 |
| 13 | −14.52 | −13.13 | −14.50 | −13.96 | −16.88 | −15.68 | −18.39 | −21.52 |
| 14 | −16.62 | −16.26 | −13.95 | −18.38 | −16.02 | −15.62 | −17.04 | −21.27 |
| 15 | −18.45 | −19.80 | −16.67 | −20.41 | −13.28 | −17.03 | −20.41 | −22.60 |
| MEAN ± SD | −15.70 ± 1.56 | −16.12 ± 2.13 | −15.59 ± 2.18 | −16.15 ± 4.61 | −16.38 ± 2.92 | −15.26 ± 2.77 | −17.03 ± 1.95 | −19.31 ± 3.62 |

TABLE VIII

Minimum temperature for site B
(a site on the subject's forearm, different from A)

| CODE | EC | ECC | FM | FMC | EI | EII | EIII | EIV |
|---|---|---|---|---|---|---|---|---|
| 1 | −17.99 | −12.79 | −15.33 | −15.36 | −19.23 | −13.00 | −17.48 | −14.42 |
| 2 | −17.03 | −17.73 | −15.35 | −18.03 | −14.68 | −16.95 | −14.87 | −19.85 |
| 3 | −13.60 | −11.70 | −14.12 | −13.34 | −13.88 | −7.89 | −16.48 | −14.30 |
| 4 | −16.89 | −16.21 | −16.35 | −12.01 | −15.75 | −10.93 | −16.93 | −19.76 |
| 5 | −15.33 | −15.84 | −13.45 | −10.33 | −15.24 | −8.25 | −13.47 | −23.14 |
| 6 | −12.73 | −15.32 | −16.29 | −12.72 | −13.62 | −10.77 | −15.14 | −12.93 |
| 7 | −15.93 | −10.04 | −10.83 | −13.86 | −15.64 | −8.89 | −14.77 | −14.93 |
| 8 | −18.79 | −20.86 | −18.79 | −20.59 | −16.41 | −16.96 | −16.34 | −22.66 |
| 9 | −12.08 | −16.69 | −13.93 | −19.34 | −11.22 | −16.24 | −16.41 | −17.74 |
| 10 | −14.03 | −18.07 | −18.01 | −19.22 | −20.83 | −18.68 | −22.58 | −19.03 |
| 11 | −18.32 | −18.65 | −13.00 | −22.26 | −25.51 | −11.30 | −14.00 | −20.84 |
| 12 | −16.52 | −10.58 | −19.36 | −15.25 | −18.53 | −16.38 | −20.94 | −20.18 |
| 13 | 16.48 | −12.08 | −19.04 | −13.88 | −16.56 | −19.48 | −18.68 | −21.70 |
| 14 | −16.02 | −17.86 | −17.82 | −20.29 | −15.28 | −16.74 | −19.38 | −16.38 |
| 15 | −17.12 | −18.69 | −18.82 | −16.51 | −17.37 | −17.71 | −23.49 | −22.35 |
| MEAN ± SD | −15.92 ± 2.01 | −15.54 ± 3.33 | −16.03 ± 2.60 | −16.25 ± 3.63 | −16.66 ± 3.40 | −14.01 ± 4.02 | −17.40 ± 3.05 | −18.68 ± 3.36 |

Tables 1 and 5 describe the experimental conditions in accordance with the procedural steps described above. The only difference between Table 1 and Table 5 and between Study 1 and Study 2 is that in Study 1 the spray time was five seconds, whereas in Study 2 the spray time was 3 seconds. Comparison is made between various coolants including ethylchloride at room temperature, ethylchloride at 11° C., Fluorimethane® at room temperature, Fuorimethane® at 11° C. and mixtures of HFC 152a and HFC 134a.

Tables 2 and 6 describe the subjects chosen including their normal skin temperature, the sex, race, age, weight and height of the subjects.

Tables 3 and 7 describe the minimum temperatures obtained for the various subjects in the two studies using the different coolants described in Tables 1 and 5. Table 3 pertains to the spray time of 5 seconds and Table 7 pertains to the spray time of 3 seconds. As can be seen, minimum temperatures obtained on site A for the HFC compositions of the present invention are very comparable to the minimum temperatures obtained using the currently available vapocoolants. No statistical difference in minimum temperatures was noted between the formulations tested.

Tables 4 and 8 detail the minimum temperatures obtained for site B for Studies 1 and 2 respectively on the various subjects, comparing the minimum temperatures between the currently available vapocoolants and the HFC vapocoolant compositions of the present invention. The minimum temperatures for the currently available vapocoolants and the minimum temperatures for mixtures EI, EIII and EIV, are very similar in magnitude to each other, i.e. no statistical difference in minimum temperatures was noted between the formulations tested. EII minimum temperatures were significantly different from EI, EIII and EIV. Thus the preferred compositions comprise between 52–55% HFC 134a (rest alcohol) and 45% HFC 152a (rest alcohol).

As pointed out above, it is important to note that the pre-injection of cooling of localized skin areas is just one of the proposed applications of the compositions of the present invention. Management of myofascial pain, restricted motion and muscle spasms and cooling of the skin prior to minor surgery are the other desired applications.

Thus it is apparent that there have been provided, in accordance with the invention, chemical compositions that fully satisfy the objects, aspects and advantages set forth above. While, the invention has been described with respect to a pair of preferred HFCs, it is evident that many alternatives, modifications and variations will be apparent to those skilled in the art in light of the foregoing description. In this respect, $CF_3CHFCF_3$, i.e. HFC 227ea (1,3 trifluoro-2-fluoro propane), would it is believed satisy all the objects, aspects and advantages set forth above. Accordingly, it is intended to embrace this and all such other alternatives, modifications, and variations which fall within the broad scope of the appended claims.

What is claimed is:

1. A non-ozone depleting, non-toxic and non-carcinogenic vapocoolant liquid chemical composition for use in localized cooling of a desired area of the skin of humans and other animals and in conjunction with the spray and stretch treatment technique, said composition:

comprising by total weight of the composition 40 to 55% hydrofluorocarbon selected from the group consisting of 1,1-difluoroethane, 1,1,1,2-tetrafluoroethane 1,3-trifluoro-2-fluoro propane, and mixtures thereof, and 60 to 45% of ethyl alcohol;

being substantially free of chlorinated fluorocarbons; and being capable of cooling said desired area to at least as low as approximately minus 5° C., upon spraying of said composition onto said desired area for a maximum of 5 seconds.

2. The vapocoolant of claim 1 further comprising upto 5% of a denaturing agent selected from the group consisting of isopropyl alcohol, acetone and camphor.

3. The vapocoolant of claim 2, wherein said hydrofluorocarbon is selected from the group consisting of 1,1-difluoroethane, 1,1,1,2-tetrafluoroethane and combinations thereof.

4. The vapocoolant of claim 3, comprising as said hydrofluorocarbon, 1,1-difluoroethane, at 45% by total weight.

5. The vapocoolant of claim 3, comprising as said hydrofluorocarbon, 1,1,1,2-tetrafluoroethane, at 52% by total weight.

6. The vapocoolant of claim 3, comprising as said hydrofluorocarbon, 1,1,1,2-tetrafluoroethane, at 55% by total weight.

7. A method of cooling the skin of a human subject comprising spraying the area of the skin to be treated with the vapocoolant of claim 1 for a period of no more than about 5 seconds such that the area of skin is cooled to at least as low as approximately −5° C.

8. A method for the management of myofascial pain syndrome utilizing the spray and stretch treatment technique comprising spraying the area of skin to be treated with the vapocoolant of claim 1 for a period of no more than about 5 seconds such that the area of skin is cooled to at least as low as approximately −5° C.

9. A method for effectively freezing skin prior to minor skin surgery comprising spraying the area of skin to be treated with the vapocoolant of claim 1 for a period of no more than about 5 seconds such that the area of skin is cooled to at least as low as approximately −5° C.

10. A method for effectively freezing skin prior to giving painless injections comprising spraying the area of skin to be treated with the vapocoolant of claim 1 for a period of no more than about 5 seconds such that the area of skin is cooled to at least as low as approximately −5° C.

11. The vapocoolant of claim 2, comprising as said hydrofluorocarbon, 1,3-trifluoro-2-fluoro propane.

* * * * *

UNITED STATES PATENT AND TRADEMARK OFFICE
CERTIFICATE OF CORRECTION

PATENT NO. : 6,737,041 B1  Page 1 of 1
DATED : May 18, 2004
INVENTOR(S) : Hussain et al.

It is certified that error appears in the above-identified patent and that said Letters Patent is hereby corrected as shown below:

Title page,
Item [*] Notice, delete "[*] Notice: Subject to any disclaimer, the term of this patent is extended or adjusted under 35 U.S.C. 154(b) by 1,826 days."

Signed and Sealed this

Fourteenth Day of September, 2004

JON W. DUDAS
*Director of the United States Patent and Trademark Office*